US00PP24950P3

(12) United States Plant Patent
Ackerman et al.

(10) Patent No.: US PP24,950 P3
(45) Date of Patent: Oct. 7, 2014

(54) STRAWBERRY PLANT NAMED 'TRIUMPH'

(50) Latin Name: *Fragaria ananassa*
Varietal Denomination: TRIUMPH

(71) Applicant: Plant Sciences, Inc., Watsonville, CA (US)

(72) Inventors: Stephen M. Ackerman, Salinas, CA (US); Steven D. Nelson, Watsonville, CA (US); Michael D. Nelson, Watsonville, CA (US)

(73) Assignee: Plant Sciences, Inc., Watsonville, CA (US)

( * ) Notice: Subject to any disclaimer, the term of this patent is extended or adjusted under 35 U.S.C. 154(b) by 84 days.

(21) Appl. No.: 13/694,410

(22) Filed: Nov. 30, 2012

(65) Prior Publication Data

US 2014/0157465 P1 Jun. 5, 2014

(51) Int. Cl.
*A01H 5/00* (2006.01)

(52) U.S. Cl.
USPC ..... Plt./209

(58) Field of Classification Search
CPC ..... A01H 1/00; A01H 1/04; A01H 1/06; A01H 4/00; A01H 4/05; A01H 4/008; A01H 5/08; A01H 5/0893
USPC ..... Plt./209
See application file for complete search history.

*Primary Examiner* — Annette Para
(74) *Attorney, Agent, or Firm* — Foley & Lardner LLP

(57) ABSTRACT

This invention relates to a new and distinct variety of strawberry plant named 'TRIUMPH'. This new strawberry plant named 'TRIUMPH' is primarily adapted to the growing conditions of the central coast of California, and is primarily characterized by its medium to large plant size, occasional fourth leaflet per tri-foliate, moderate to heavy petiole pubescence, medium to long fruiting trusses, and very attractive, medium-sized berry with good gloss, even red color and conical shape.

5 Drawing Sheets

Latin name of the genus and species of the plant claimed: *Fragaria ananassa.*

Variety denomination: 'TRIUMPH'.

BACKGROUND OF THE INVENTION

The present invention relates to a new and distinct strawberry variety named 'TRIUMPH'. This new variety is a result of a controlled cross made in 2003 in an ongoing breeding program between strawberry variety designated 'PS-3003' (non-patented selection) and strawberry variety designated 'PS-4634' (patented, U.S. Plant Pat. No. 17,487). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the fall of 2005. After its selection, the new variety was asexually propagated by stolons in both San Joaquin County, Calif. and Siskiyou County, Calif. The new variety was extensively tested over the next several years in fruiting fields in Ventura County, Calif. This propagation has demonstrated that the combination of traits disclosed herein as characterizing the new variety are fixed and remain true to type through successive generations of asexual reproduction.

BRIEF SUMMARY OF THE INVENTION

'TRIUMPH' is primarily adapted to the climate and growing conditions of the central coast of California. The nearby Pacific Ocean provides the needed humidity and moderate temperatures to produce a strong vigorous plant and maintain fruit quality during the fall production months.

The following traits have been repeatedly observed and are determined to be unique characteristics of 'TRIUMPH', which in combination distinguish this strawberry plant as a new and distinct variety:

1. Medium to large plant size;
2. Occasionally has a fourth leaflet per tri-foliate;
3. Moderate to heavy petiole pubescence;
4. Medium to long fruiting trusses; and
5. Very attractive, medium-sized berry with good gloss, even red color and conical shape.

The strawberry variety that is believed to be most closely related to the new variety 'TRIUMPH' is 'VALOR' (patented, U.S. Plant Pat. No. 20,394). In side-by-side comparisons to the similar strawberry variety 'VALOR', 'TRIUMPH' differs by the following combination of characteristics as described in Table 1.

TABLE 1

COMPARISON TO THE STANDARD VARIETY

| Characteristic | 'TRIUMPH' | 'VALOR' (US PP 20,394) |
|---|---|---|
| Fruit: color | Red | Ranges from red to dark red |
| Fruit: length × width ratio | Slightly longer than broad | As long as broad to slightly longer than broad |
| Fruit: difference in shape between primary and secondary | Slight | Moderate |

TABLE 1-continued

| COMPARISON TO THE STANDARD VARIETY | | |
|---|---|---|
| Characteristic | 'TRIUMPH' | 'VALOR' (US PP 20,394) |
| Plant: size | Ranges from medium to large | Medium |
| Stolon: attitude of hairs | Strongly outward | Upward |
| Foliage: size | Ranges from medium to large | Medium |
| Foliage: color | Medium green | Ranges from medium to dark green |
| Foliage: number of leaflets | Ranges from three to four | Three |
| Petiole: pubescence | Ranges from moderate to heavy | Sparse |
| Fruiting truss: length | Ranges from medium to long | Medium |
| Pedicel: attitude of hairs | Strongly outward | Upward |

For identification, a series of molecular markers have been determined for this new variety.

'TRIUMPH' differs from its parents, 'PS-3003' and 'PS-4634', by the following combination of characteristics as described in Table 2.

TABLE 2

| COMPARISON TO THE PARENT VARIETIES | | | |
|---|---|---|---|
| Characteristic | 'TRIUMPH' | 'PS-3003' | 'PS-4634' (US PP 17,487) |
| Fruit color | Red | Light red | Ranges from orange red to red |
| Plant size | Ranges from medium to large | Medium | Large |
| Type of bearing | Everbearing | Everbearing | Summer bearing |
| Runner production (nursery) | Medium | Ranges from medium to light | Many |

BRIEF DESCRIPTIONS OF THE PHOTOGRAPHS

The accompanying color photographs illustrate the overall appearance of typical specimens of the new strawberry variety 'TRIUMPH', at various stages of development as true as it is reasonably possible with color reproductions of this type. Color in the photographs may differ slightly from the color value cited in the botanical descriptions which accurately describe the color of 'TRIUMPH'. The depicted plant and plant parts of the new strawberry variety 'TRIUMPH' are between three and four months old. The photographs were taken in Ventura County, Calif.:

DETAILED BOTANICAL DESCRIPTION

Figure 1:
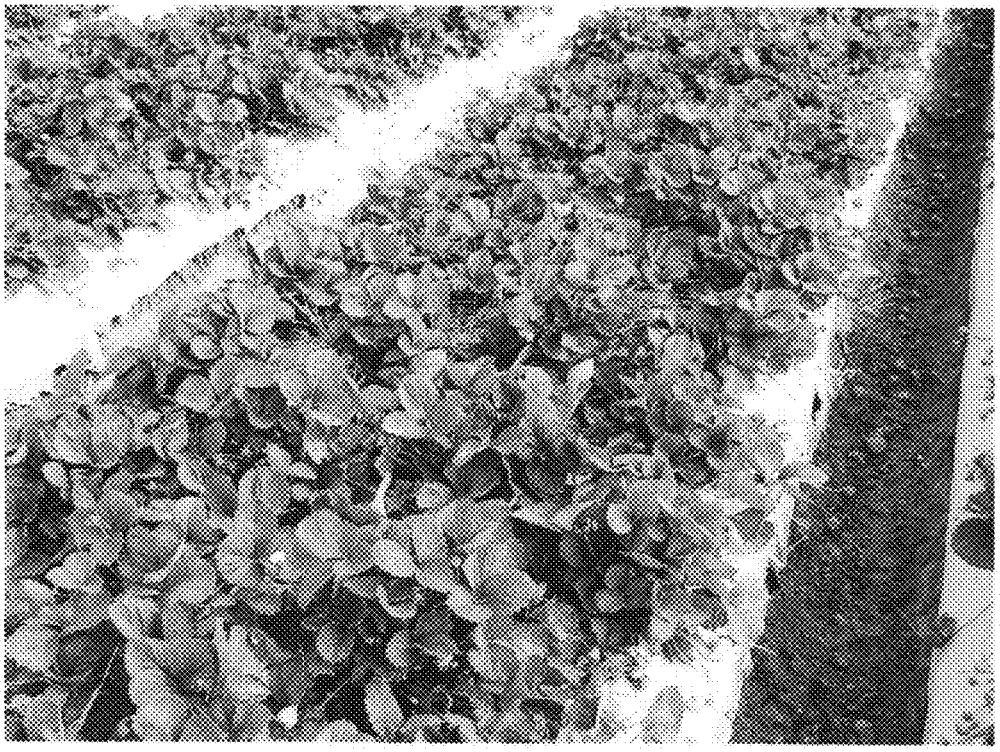
FIG. 1 shows typical fruiting field characteristics of 'TRIUMPH', taken in the month of November 2012.
Figure 2:
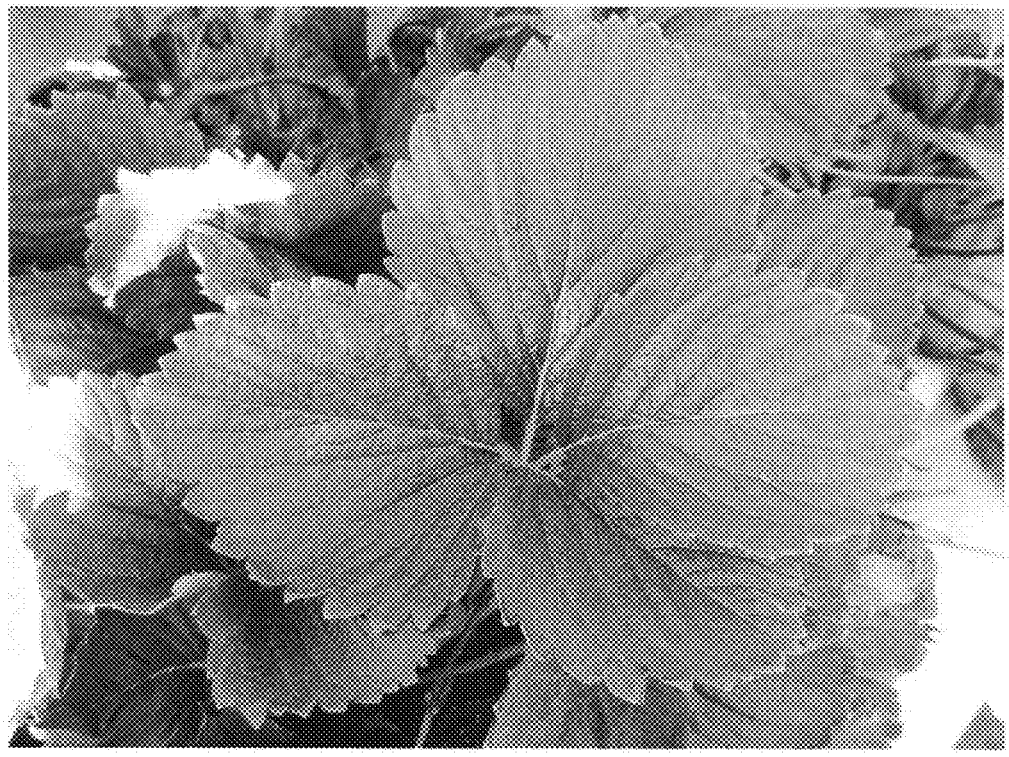
FIG. 2 shows a close-up view of the typical leaf structure of 'TRIUMPH', taken in the month of October 2012.
Figure 3:
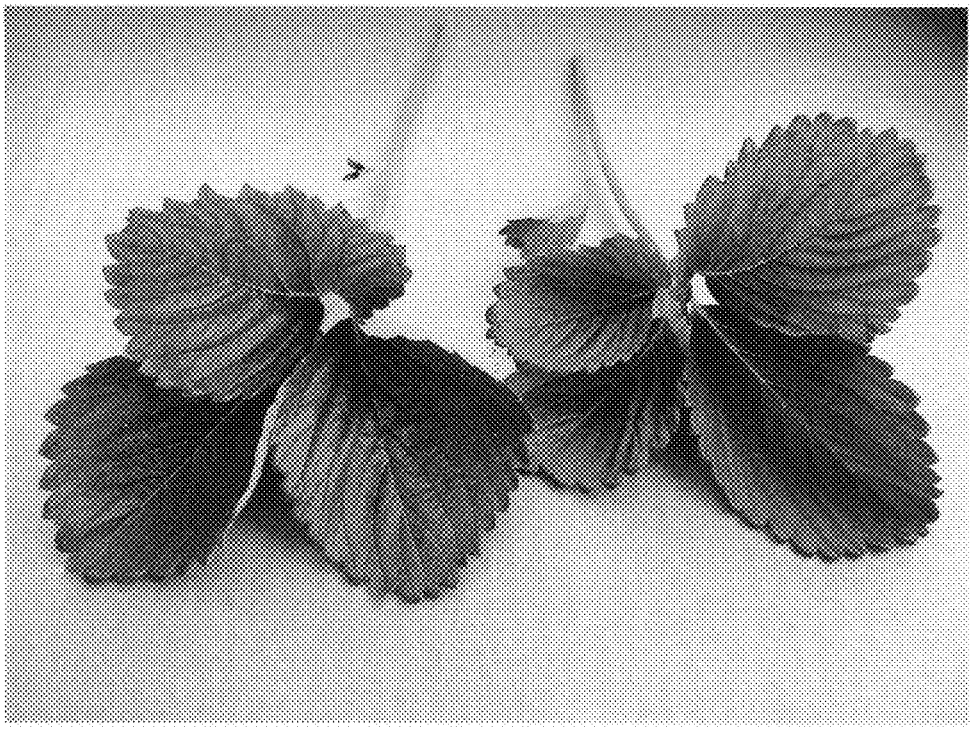
FIG. 3 shows a close-up view comparing leaf structure of 'TRIUMPH', taken in the month of October 2012.
Figure 4:
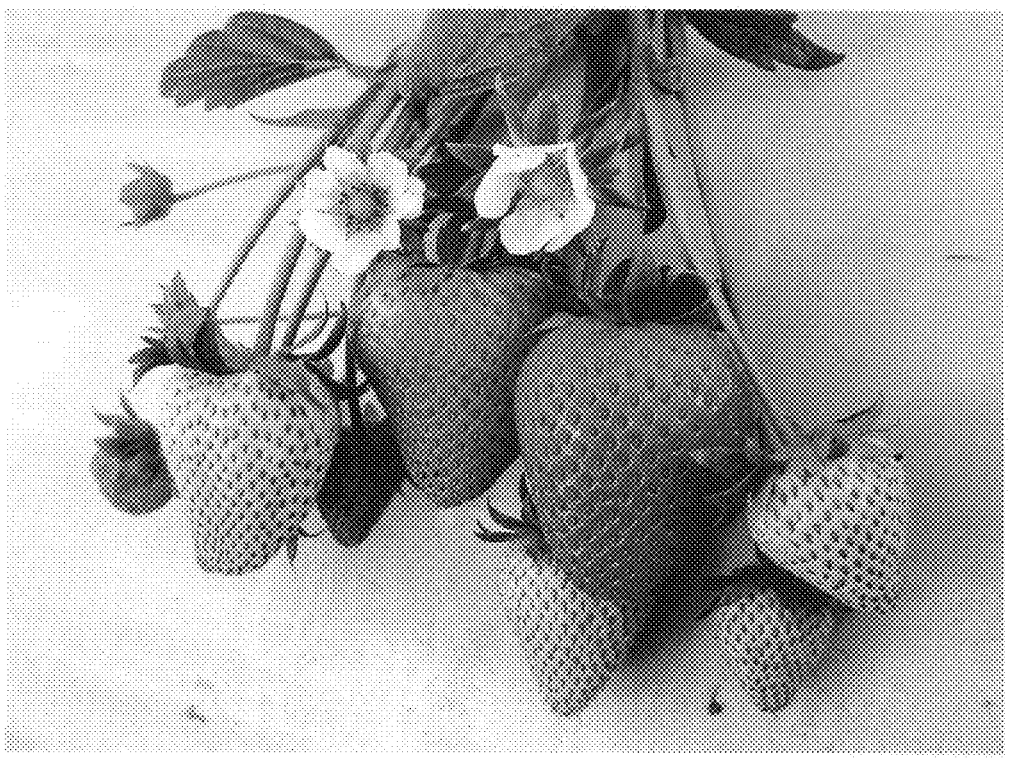
FIG. 4 shows typical mature and immature field fruit of 'TRIUMPH', taken in the month of October 2012.
Figure 5:
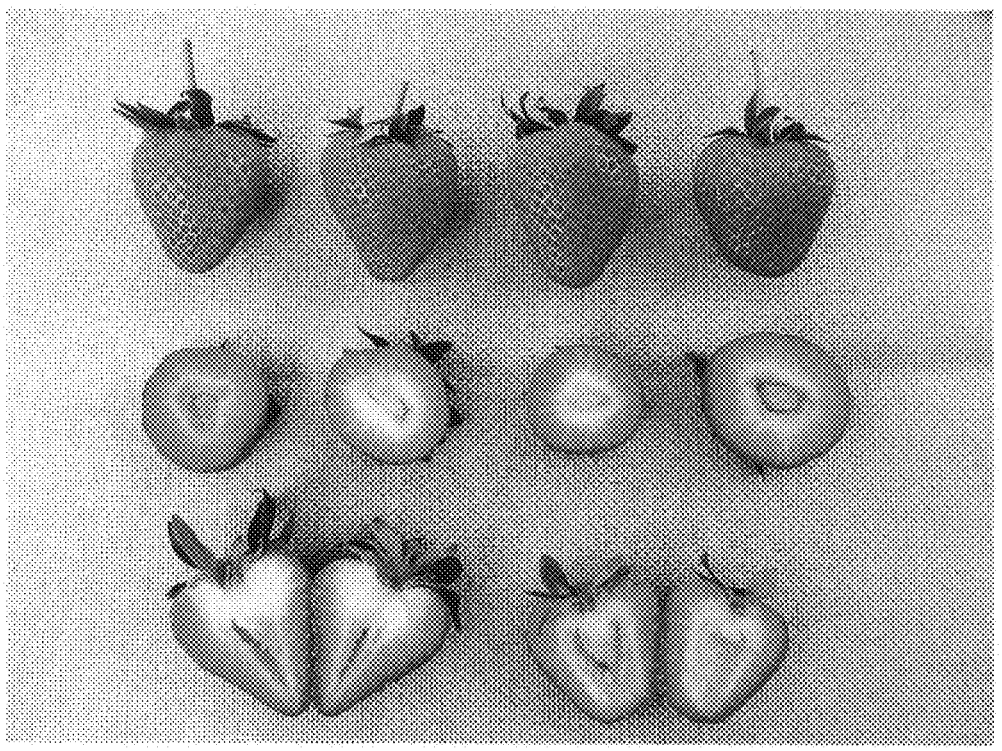
FIG. 5 shows typical internal and external mature fruit characteristics of 'TRIUMPH', taken in the month of November 2012.

The new variety 'TRIUMPH' has not been observed under all possible environmental conditions. The characteristics of the new variety 'TRIUMPH' may vary in detail, depending upon variations in environmental factors, including weather (temperature, humidity and light intensity), day length, soil type and location. In addition, the characteristics of any parental variety or comparison variety included in Tables 1-9 of the present invention may vary in detail, depending upon variations in environmental factors, including weather (temperature, humidity and light intensity), day length, soil type and location.

The aforementioned photographs, together with the following description of the new variety 'TRIUMPH', unless otherwise noted, are based on observations taken during the 2012 growing season in Ventura County, Calif. These measurements and ratings were taken from plants of 'TRIUMPH' dug from a low-elevation nursery located in San Joaquin County, Calif. during January 2012 and planted six months later in Ventura County, Calif. The approximate age of the observed plants is between three and four months. Yield observations and fruit quality characteristics are averaged from four years of data collected from the 2008 through 2011 growing seasons. Flower measurements and characteristics are from secondary flowers unless otherwise noted. Fruit characteristics and measurements are from secondary fruit unless otherwise noted.

Color terminology where noted follows The Royal Horticultural Society Colour Chart, London (2007).

The following tables 3 through 9 describe fruit, plant, stolon, foliage, fruiting truss, flower and pest disease characteristics of the new strawberry 'TRIUMPH' in comparison to the similar strawberry variety 'VALOR'.

TABLE 3

| FRUIT CHARACTERISTICS | | |
|---|---|---|
| Characteristic | 'TRIUMPH' | 'VALOR' (US PP 20,394) |
| Color of mature fruit | RHS 44A Red | RHS 46A Ranges from red to dark red |
| Color of internal flesh | RHS 44B Medium red | RHS 45A Ranges from medium red to dark red |
| Color of core | RHS 44C Light red | RHS 45B Medium red |
| Fruit length (cm) | 4.3 | 3.7 |
| Fruit width (cm) | 3.6 | 3.5 |
| Fruit length/width ratio | 1.24 Slightly longer than broad | 1.05 Slightly longer than broad |
| Calyx diameter (cm) | 4.9 | 4.7 |
| Average fruit weight (gm) | 21.5 | 22.0 |
| Achene color, shaded side | RHS 160A Greyed yellow group | RHS 160A Greyed yellow group |
| Achene color, sun-exposed side | RHS 182A Greyed red group | RHS 183A Greyed red group |
| Achenes per berry | 311 | 382 |
| Achene weight (mg) | 0.62 | 0.43 |
| Marketable fruit yield (gm/plant) | 583 | 528 |
| Fruit size | Medium | Ranges from medium to large |
| Predominant fruit shape | Conical | Conical |
| Difference in shapes between primary and secondary fruit | Slight | Ranges from slight to moderate |
| Band without achenes | Absent or very narrow | Absent or very narrow |

TABLE 3-continued

| FRUIT CHARACTERISTICS | | |
|---|---|---|
| Characteristic | 'TRIUMPH' | 'VALOR' (US PP 20,394) |
| Unevenness of fruit surface | Weak | Weak |
| Evenness of fruit color | Even | Even |
| Fruit glossiness | Ranges from medium to strong | Ranges from medium to strong |
| Insertion of achenes | Level with surface | Ranges from below surface to level with surface |
| Insertion of calyx | In the basin | In the basin |
| Attitude of calyx | Spreading | Spreading |
| Size of calyx in relation to fruit diameter | Slightly larger | Slightly larger |
| Adherence of calyx | Strong | Strong |
| Firmness of fruit flesh | Ranges from medium to firm | Firm |
| Keeping quality | Very good | Very good |
| Distribution of red color of the flesh | Marginal and central | Marginal and central |
| Hollow center expression | Weak | Absent or very weak |
| Fruit flavor | Ranges from very good to good | Good |
| Soluble solids (% brix) | 7.3 | 7.6 |
| Time of first flowering | Early | Ranges from early to medium |
| Time of first harvesting | Early | Ranges from early to medium |
| Harvest period | Late September to mid December | Late September to mid December |
| Type of bearing | Fully remontant (everbearing) | Fully remontant (everbearing) |

TABLE 4

| PLANT CHARACTERISTICS | | |
|---|---|---|
| Characteristic | 'TRIUMPH' | 'VALOR' (US PP 20,394) |
| Plant height (cm) | 25.8 | 23.0 |
| Plant spread (cm) | 35.4 | 29.9 |
| Crowns per plant | 3.5 | 5.3 |
| Plant size | Large | Medium |
| Plant habit | Upright | Upright |
| Plant density | Medium | Medium |
| Plant vigor | Strong | Medium |

TABLE 5

| STOLON CHARACTERISTICS | | |
|---|---|---|
| Characteristic | 'TRIUMPH' | 'VALOR' (US PP 20,394) |
| Stolon color | RHS 146C Yellow green group | RHS 144A Yellow green group |
| Stolon anthocyanin coloration | RHS 180C Greyed red group | RHS 180A Greyed red group |
| Stolon anthocyanin intensity | Weak | Ranges from weak to medium |
| Stolon pubescence | Dense | Dense |
| Attitude of hairs | Strongly outward | Upward |
| Average stolon quantity (nursery) | Medium | Few |
| Average stolon diameter at bract (mm) | 3.4 | 3.3 |

TABLE 6

| FOLIAGE CHARACTERISTICS | | |
|---|---|---|
| Characteristic | 'TRIUMPH' | 'VALOR' (US PP 20,394) |
| Foliage: | | |
| Color of upper surface | RHS 137A Medium green | RHS N 137B Ranges from medium green to dark green |
| Color of underside | RHS 147C Yellow green group | RHS 147C Yellow green group |
| Number of leaflets | Ranges from 3 to 4 | 3 |
| Shape in cross section | Slightly concave | Slightly concave to flat |
| Interveinal blistering | Medium | Medium |
| Leaf glossiness | Medium | Medium |
| Leaf variegation | Present | Present |
| Terminal Leaflet: | | |
| Length (cm) | 9.7 | 7.7 |
| Width (cm) | 8.3 | 8.0 |
| Leaf size | Ranges from large to medium | Medium |
| Length/width ratio | 1.18 Longer than broad | 0.97 As long as broad |
| Shape of base | Acute | Obtuse |
| Shape of teeth | Obtuse | Obtuse |
| Serrations per leaf | 22.5 | 20.3 |
| Petiole: | | |
| Petiole color | RHS 146C Yellow green group | RHS 144A Yellow green group |
| Petiole length (cm) | 18.7 | 16.3 |
| Petiole diameter (mm) | 3.8 | 3.8 |
| Petiolule color | RHS 146C Yellow green group | RHS 144A Yellow green group |
| Petiolule length (mm) | 16.4 | 12.4 |
| Attitude of hairs | Slightly outward | Slightly outward |
| Petiole pubescence | Ranges from heavy to moderate | Sparse |
| Stipule: | | |
| Color | 146C Yellow green group | 146A Yellow green group |
| Anthocyanin coloration | None | RHS 61A Red purple group |
| Anthocyanin intensity | Absent or very weak | Weak |
| Length (mm) | 18.8 | 18.8 |
| Width (mm) | 9.5 | 10.8 |

TABLE 7

| FRUITING TRUSS CHARACTERISTICS | | |
|---|---|---|
| Characteristic | 'TRIUMPH' | 'VALOR' (US PP 20,394) |
| Anthocyanin coloration | RHS 181D Greyed red group | RHS 181C Greyed red group |
| Anthocyanin intensity | Absent or very weak | Absent or very weak |
| Length at maturity (cm) | 32.4 | 28.4 |
| Position relative to foliage | Ranges from beneath to level with | Level with |
| Number of flowers | Medium | Medium |
| Pedicel attitude of hairs | Strongly outward | Upward |
| Pubescence | Strong | Ranges from medium to strong |
| Attitude at first pick | Prostrate | Prostrate |

TABLE 8

| FLOWER CHARACTERISTICS | | |
|---|---|---|
| Characteristic | 'TRIUMPH' | 'VALOR' (US PP 20,394) |
| Petal color | RHS NN 155C White group | RHS NN 155C White group |
| Sepal color | RHS 137B Green group | RHS 137A Green group |
| Receptacle color | RHS 147C Green group | RHS 147C Green group |
| Anther color | RHS 15A Yellow orange group | RHS 14B Yellow orange group |
| Corolla diameter (mm) | 32.0 Medium | 29.8 Medium |
| Calyx diameter (mm) | 36.0 | 31.7 |
| Petal length (mm) | 11.7 | 12.0 |
| Petal width (mm) | 11.6 | 11.7 |
| Petal length/width ratio | 1.01 As long as broad | 1.03 As long as broad |
| Petals/flower | 6.4 | 6.0 |
| Sepal length (mm) | 13.7 | 13.8 |
| Sepal width (mm) | 5.3 | 6.4 |
| Sepal length/width ratio | 2.60 | 2.18 |
| Sepals/flower | 13.6 | 12.3 |

TABLE 8-continued

| FLOWER CHARACTERISTICS | | |
|---|---|---|
| Characteristic | 'TRIUMPH' | 'VALOR' (US PP 20,394) |
| Size of calyx relative to corolla | Larger | Larger |
| Stamen | Present | Present |
| Size of inner calyx relative to outer calyx | Ranges from smaller to same | Smaller |
| Relative position of petals | Overlapping | Ranges from touching to overlapping |

TABLE 9

| PEST AND DISEASE REACTIONS | | |
|---|---|---|
| Characteristic | 'TRIUMPH' | 'VALOR' (US PP 20,394) |
| Powdery mildew | Susceptible | Susceptible |
| Angular leaf spot | Moderately susceptible | Moderately susceptible |
| Botrytis fruit rot | Moderately susceptible | Moderately susceptible |
| Two-spotted spider mite | Moderately susceptible | Moderately susceptible |
| Lygus bug | Susceptible | Susceptible |
| Flower thrips | Moderately resistant | Moderately susceptible |

We claim:

1. A new and distinct strawberry plant named 'TRIUMPH', as herein described and illustrated by the characteristics set forth above.

* * * * *